(12) United States Patent
Hansen et al.

(10) Patent No.: US 12,064,370 B2
(45) Date of Patent: Aug. 20, 2024

(54) MEDICAL SYSTEM, ACCESSORY DEVICE, AND RELATED METHODS

(71) Applicant: Coloplast A/S, Humlebaek (DK)

(72) Inventors: Jais Ask Hansen, Jaegerspris (DK);
Lars Erup Larsen, Maaloev (DK);
Finn Speiermann, Virum (DK); Niels Hvid, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 989 days.

(21) Appl. No.: 16/979,526

(22) PCT Filed: Mar. 15, 2019

(86) PCT No.: PCT/DK2019/050088
§ 371 (c)(1),
(2) Date: Sep. 10, 2020

(87) PCT Pub. No.: WO2019/174694
PCT Pub. Date: Sep. 19, 2019

(65) Prior Publication Data
US 2021/0000633 A1    Jan. 7, 2021

(30) Foreign Application Priority Data
Mar. 15, 2018  (DK) ............. PA 2018 70161

(51) Int. Cl.
*A61F 5/44*    (2006.01)
*A61F 5/443*   (2006.01)
(Continued)

(52) U.S. Cl.
CPC ............ *A61F 5/4404* (2013.01); *A61F 5/443* (2013.01); *G01C 19/00* (2013.01); *G01K 13/00* (2013.01); *G01P 15/00* (2013.01); *G01R 33/02* (2013.01)

(58) Field of Classification Search
CPC ........ A61F 5/443; A61F 5/448; A61F 5/4404; A61F 5/445; G16H 10/60; G16H 40/67;
(Continued)

(56) References Cited

U.S. PATENT DOCUMENTS

| 6,171,289 B1 | 1/2001 | Millot et al. | |
| 2013/0324952 A1* | 12/2013 | Krystek | A61F 5/445 |
| | | | 604/318 |

(Continued)

*Primary Examiner* — Dionne Pendleton
(74) *Attorney, Agent, or Firm* — Coloplast Corp., Coloplast A/S; Nick Baumann

(57) ABSTRACT

A method and an accessory device for an ostomy system comprising a monitor device and an ostomy appliance, the ostomy appliance comprising a base plate is disclosed. The accessory device comprises a memory; a processor; and an interface coupled to the processor and configured to communicate with the monitor device, wherein the interface comprises a display and is configured to obtain monitor data from the monitor device coupled to the ostomy appliance, the monitor data comprising sensor data and one or more of ostomy data obtained from electrodes of the base plate, and parameter data based on ostomy data obtained from electrodes of the base plate, the sensor data obtained from one or more sensors in the monitor device, wherein the processor is configured to determine an operating state of the base plate based on the sensor data and one or more of ostomy data and parameter data based on ostomy data; and display, on the display, a first user interface comprising a first user interface object representing the operating state of the base plate.

12 Claims, 14 Drawing Sheets

(51) Int. Cl.
*G01C 19/00* (2013.01)
*G01K 13/00* (2021.01)
*G01P 15/00* (2006.01)
*G01R 33/02* (2006.01)

(58) Field of Classification Search
CPC ..... G16H 80/00; G01M 3/165; A61B 5/4851; A61B 2560/0204; A61B 2560/0487; A61B 2562/0219; A61B 2562/0271; A61B 2562/029; A61B 5/01; A61B 5/6813; A61B 5/6833; A61B 5/742; A61B 5/7435; G01C 19/00; G01K 13/00; G01P 15/00; G01R 33/02; H04M 1/72409; G09G 2380/08; G05B 2219/32128; B23K 2103/42; B23K 2103/50; B23K 26/402
See application file for complete search history.

(56) References Cited

U.S. PATENT DOCUMENTS

| | | | |
|---|---|---|---|
| 2016/0158056 A1* | 6/2016 | Davis | A61F 5/443 29/872 |
| 2017/0140103 A1* | 5/2017 | Angelides | A61F 5/4404 |
| 2017/0340474 A1 | 11/2017 | Thirstrup et al. | |

* cited by examiner

MEDICAL SYSTEM, ACCESSORY DEVICE, AND RELATED METHODS

The present disclosure relates to an ostomy system and devices thereof. The ostomy system comprises an ostomy appliance and a monitor device. In particular, the present disclosure relates to an accessory device and related method, e.g. for monitoring and communicating an operating state of the base plate based on sensor data of the monitor device.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
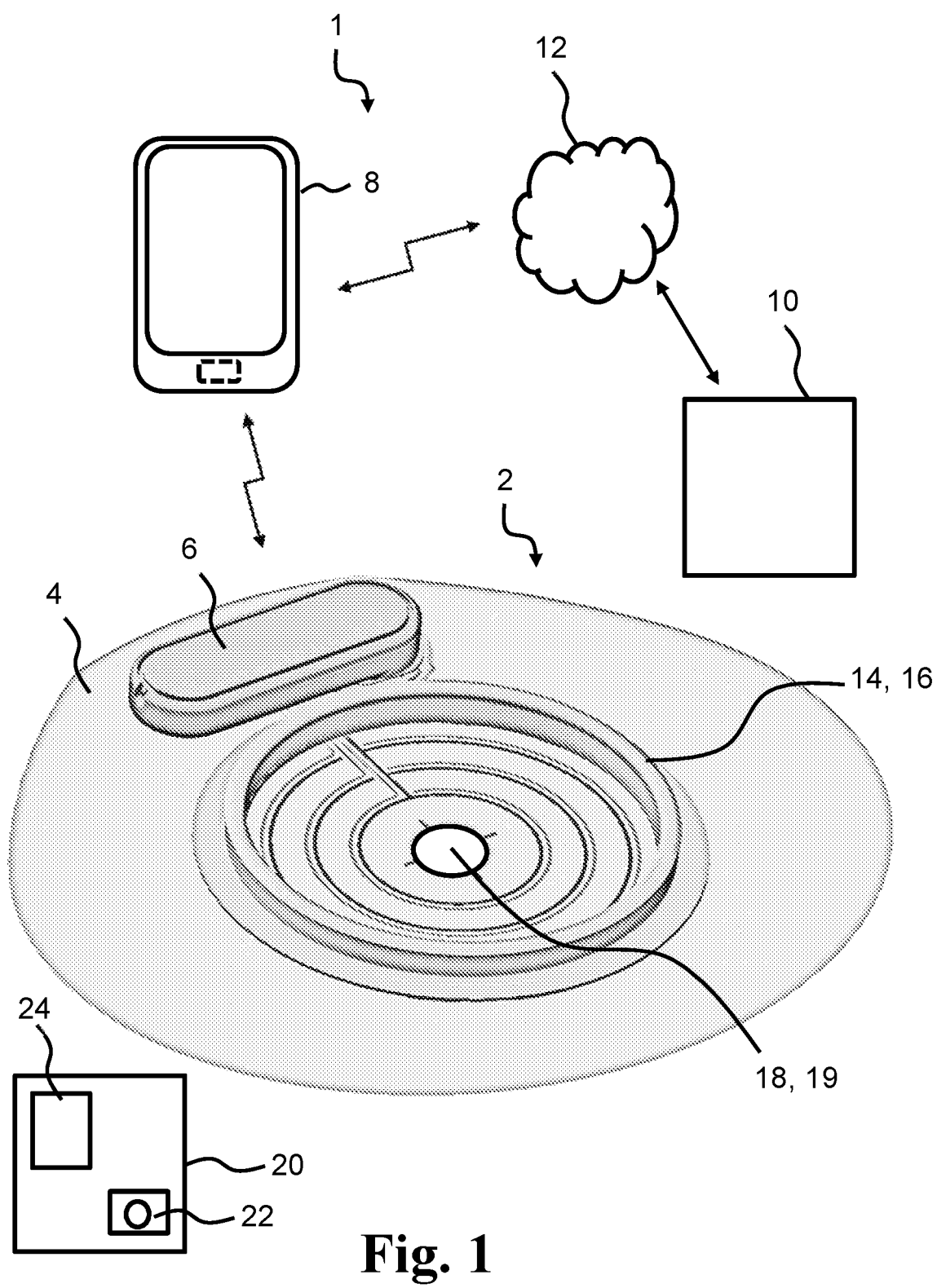
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface when a user wears the ostomy appliance/monitor device. Likewise, whenever referring to the distal side or surface of a layer, an element, a device or part of a device, the referral is to the side or surface facing away from the skin when a user wears the ostomy appliance/monitor device. In other words, the proximal side or surface is the side or surface closest to the user when the appliance is fitted on a user and the distal side is the opposite side or surface—the side or surface furthest away from the user in use.

The axial direction is defined as the direction of the stoma when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

An ostomy system comprising an ostomy appliance and a monitor device, the ostomy appliance comprising a base plate is disclosed, wherein the monitor device is a monitor device as described herein.

An ostomy system comprising a monitor device and an ostomy appliance comprising a base plate is disclosed, the base plate having a first adhesive layer with a proximal side configured for attachment of the base plate to the skin surface of a user, the first adhesive layer having a stomal opening with a center point, the monitor device comprising a processor and a sensor unit comprising a first sensor with a first sensor surface accommodated in a monitor device housing, the monitor device housing having a sensor opening in a proximal surface of the monitor device, the sensor opening forming at least a part of a sensor path from surroundings of the proximal surface to the first sensor surface.

Also disclosed is a monitor device for an ostomy appliance of an ostomy system, the monitor device comprising a processor and a sensor unit comprising a first sensor with a first sensor surface accommodated in a monitor device housing, the monitor device housing having a sensor opening in a proximal surface of the monitor device, the proximal surface configured for facing the skin of a user during use, the sensor opening forming at least a part of a sensor path from surroundings of the proximal surface to the first sensor surface.

The present disclosure provides an ostomy system and devices thereof, such as an ostomy appliance, a base plate for an ostomy appliance, a monitor device, and optionally one or more accessory devices which either alone or together may facilitate reliable monitoring of the ostomy appliance.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. due to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

A base plate for an ostomy appliance is disclosed, the base plate comprising a first adhesive layer with a proximal side configured for attachment of the base plate to the skin surface of a user, the first adhesive layer having a stomal opening with a center point; and a plurality of electrodes including a ground electrode, a first electrode, and a optionally a second electrode, the ground electrode comprising a ground connection part, the first electrode comprising a first connection part, and the second electrode comprising a second connection part, wherein the ground electrode forms a ground for the first electrode and/or the second electrode.

The base plate comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer has a stomal opening with a center point or is at least prepared for forming a stomal opening with a center point. A base plate with three electrodes having sensing parts with contact to the first adhesive layer allows for determining erosion/swelling properties or characteristics of the first adhesive layer and/or determining a degree of erosion and/or swelling of the first adhesive layer.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance.

Further, determination of operating state and classification of operating states of the base plate is useful in helping to reduce the risk of a user experiencing leakage from an ostomy appliance, e.g. between the skin and the base plate. Further, determination of operating state and classification of operating states of the base plate is further useful in helping reduce the risk of skin damage to a user. In particular, determination of operating state according to the present disclosure may help provide a clear distinction or differentiation between adhesive failure, leakage of output, which is harmful to the skin, and a sweating ostomate.

The present disclosure provides a simple, efficient, and easy-to-use ostomy appliance system with a high degree of comfort for a user.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is configured to overlap a (sensing) part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap (sensing) parts of an electrode and the primary second sensor point openings configured to overlap (sensing) parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap (sensing) parts of an electrode and the tertiary second sensor point openings configured to overlap (sensing) parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground or reference for the first electrode. The ground electrode may comprise a second electrode part. The second electrode part of the ground electrode may form a ground or reference for the second electrode. The ground electrode may comprise a third electrode part. The third electrode part of the ground electrode may form a ground or reference for the third electrode. The ground electrode may comprise a fourth electrode part. The fourth electrode part of the ground electrode may form a ground or reference for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allows for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop, and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. Thus, one or more electrodes may be arranged between the support layer and the first adhesive layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a (sensing) part of the ground electrode and/or a (sensing) part of the fourth electrode. A secondary sensor point opening may overlap a (sensing) part of the fourth electrode and/or a (sensing) part of the fifth electrode. A tertiary sensor point opening may overlap a (sensing) part of the fifth electrode and/or a (sensing) part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode.

The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor. The processor controls the operation of the monitor device including collection and processing of ostomy data from the base plate of the ostomy appliance, processing of, such as storing, sensor data from sensor unit, and generation/transmission of monitor data to accessory devices.

The monitor device comprises a memory for storing ostomy data and/or parameter data based on the ostomy data. The processor may be configured for processing and storing sensor data in the memory.

The monitor device comprises a monitor device housing optionally made of a plastic material. The monitor device housing may be an elongate housing having a first end and a second end. The monitor device housing may have a length or maximum extension along a longitudinal axis in the range from 1 cm to 10 cm. The monitor device housing may have a width or maximum extension perpendicular to the longitudinal axis in the range from 0.5 cm to 5 cm, such as from 0.8 cm to 3 cm. The monitor device housing may be curve-shaped.

The monitor device housing may have a plurality of sensor openings, e.g. a plurality of sensor openings for a sensor and/or a sensor opening for each of a plurality of sensors.

The monitor device may comprise one or more sensor openings in a distal surface of the monitor device. The monitor device may comprise one or more sensor openings in a side surface of the monitor device. The monitor device may comprise one or more sensor openings in an end surface of the monitor device.

The sensor opening in the proximal surface is arranged at a sensor opening distance from the first end. The sensor opening distance, also denoted $D\_S$, may be in the range from 0.25 L to 0.75 L, such as from 0.35 L to 0.65 L, where L is the length of the monitor device housing. The sensor opening distance may be in the range from 10 mm to 70 mm.

The monitor device housing comprises or forms a sensor path from surroundings of the proximal surface to the first sensor surface. The sensor path translates temperature and/or humidity at the proximal surface of the monitor device/monitor device housing to the first sensor surface. The sensor opening forms a part of the sensor path and has a cross-sectional area optionally in the range from 0.2 $mm^2$ to 10 $mm^2$. The sensor opening may be a circular sensor opening with a diameter in the range from 0.3 mm to 1.4 mm, e.g. from 0.6 mm to 1.0 mm.

The monitor device comprises a sensor unit with one or more sensors including a first sensor. The sensor unit is connected to the processor for feeding sensor data to the processor. The sensor unit may comprise a humidity sensor for provision of humidity data to the processor. Thus, the sensor data may comprise humidity data. For example, the first sensor may be a humidity sensor for provision of humidity data to the processor. Thus, the present disclosure enables humidity detection near the skin of a user and/or on the distal side of the base plate, which in turn can be used for a more accurate estimation of base plate operation state.

The sensor unit may comprise a temperature sensor for provision of temperature data to the processor. Thus, the sensor data may comprise temperature data. For example, the first sensor may be a temperature sensor for provision of temperature data to the processor. Thus, the present disclosure enables temperature detection near the skin of a user and/or on the distal side of the base plate, which in turn can be used for a more accurate estimation of base plate operation state.

The first sensor may be a combined humidity and temperature sensor for provision of humidity and temperature data to the processor.

The sensor unit of the monitor device may comprise a second sensor, e.g. an accelerometer for provision of acceleration data to the processor. The sensor unit of the monitor device may comprise a third sensor, e.g. a gyroscope for provision of gyroscope data to the processor. The sensor unit of the monitor device may comprise a fourth sensor, e.g. a magnetometer for provision of magnetometer data to the processor.

The processor is configured for processing ostomy data obtained from the base plate and generate or determine monitor data that are transmitted to an accessory device. The monitor data may comprise sensor data obtained from the sensor unit.

The monitor device comprises a first interface for connecting the monitor device to the base plate. The first interface may be arranged in the proximal surface of the monitor device housing. The first interface may be arranged within a first interface distance from the first end. The first interface distance may be less than 0.50 L, such as less than 0.4 L, where L is the length of the monitor device housing.

The monitor device may comprise a sealing element forming a seal between the first sensor and a housing part of the monitor device housing. The sealing element may be an O-ring, e.g. made of a rubber material. The sealing element may encircle the first sensor surface to expose the first sensor surface (membrane) to the sensor path while providing a closed cavity of the monitor device, the closed cavity accommodating PCB, processor, and other electronic circuitry. A glue may form the sealing element.

The ostomy system enables a reliable and accurate measurement of different parameters relevant for monitoring of the ostomy appliance. In the ostomy system, a distance between the proximal surface of the monitor device and a distal surface of the base plate, in a coupled state, is in the range from 0.2 mm to 10 mm, such as in the range from 0.5 mm to 5 mm. In the coupled state, the monitor device is attached to the base plate and arranged in its intended position during use of the ostomy system.

The monitor device comprises a first interface connected to the processor. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively. The processor may be configured to transmit monitor data, as a wireless monitor signal via the antenna and the wireless transceiver.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The accessory device comprises a memory, a processor, and an interface coupled to the processor. The interface comprises a display, such as a touch-sensitive display, and a transceiver unit.

The interface/transceiver unit of the accessory device is configured to communicate with monitor device and/or server device. The interface of the accessory device may be configured to communicate with server device via a network.

The interface of the accessory device may be configured as a monitor interface for connecting, e.g. wirelessly connecting, the accessory device to one or more monitor devices. The interface of the accessory device may comprise a transceiver unit, e.g. including an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5.

The accessory device is configured to receive monitor data from one or more monitor devices. The accessory device may be configured to transmit accessory data, e.g. to a server device. For example, the processor of the accessory device may be configured to transmit accessory data, as a wireless accessory signal via the antenna and the wireless transceiver.

The interface of the accessory device comprises a display. The interface of the accessory device is configured to obtain monitor data from the monitor device coupled to the ostomy appliance, e.g. via the transceiver unit. The monitor data may comprise sensor data obtained from one or more sensors in the monitor device. The monitor data may comprise ostomy data obtained from electrodes of the base plate, and/or parameter data based on ostomy data obtained from electrodes of the base plate. The parameter data may be indicative of voltage between respective electrode pairs of the base plate (and thus indicative of resistance). The parameter data may be indicative of current between respective electrode pairs of the base plate (and thus indicative of resistance).

The monitor data may be indicative of a condition or operating state of the ostomy appliance, e.g. a condition or operating state of the base plate disclosed herein. The condition or operating state of the ostomy appliance or of the base plate disclosed herein may refer to a level of a physical property of at least a part of the ostomy appliance, such as a level of moisture and/or temperature of at least a part of the base plate, such as a level of a physical property of at least a layer of the base plate, such as a level of moisture and/or temperature of at least a layer of the base plate, such as a level of a physical property of at least an adhesive layer of the base plate (e.g. a first adhesive layer proximal to the skin of the user). In one or more exemplary accessory devices, the interface is configured to obtain the monitor data by obtaining the monitor data indicative of the condition or operating state comprising a moisture level of a first adhesive layer of the base plate and/or a moisture level of a proximal side of the first adhesive layer. The moisture level may be seen as representative of a conductive path in the first adhesive layer, such as across the first adhesive layer. The monitor data comprises e.g. data representative of the measurement of the electrical properties of the first adhesive layer. In other words, the condition may be seen as a condition of the first adhesive layer.

A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first user interface object. A user interface object, such as the first user interface object may represent an operating state of the base plate.

An accessory device is disclosed, e.g. for or of an ostomy system comprising a monitor device and an ostomy appliance, the ostomy appliance comprising a base plate. The accessory device comprises a memory; a processor; and an interface coupled to the processor and configured to communicate with the monitor device. The interface comprises a display and is configured to obtain monitor data from the monitor device coupled to the ostomy appliance, the monitor data comprising sensor data. The monitor data optionally comprises one or more of ostomy data obtained from electrodes of the base plate, and parameter data based on ostomy data obtained from electrodes of the base plate. The sensor data are obtained from one or more sensors in the monitor device.

The processor of the accessory device is configured to determine an operating state of the base plate based on the sensor data and/or one or more of ostomy data and parameter data based on ostomy data; and display, on the display, a first user interface comprising a first user interface object representing the operating state of the base plate.

Determination of operating state of the base plate based on both ostomy data/parameter data and sensor data of the monitor device allows for improved operating state determination by enabling improved classification of moisture patterns (adhesive performance) and moisture propagation in adhesive layer(s) of the base plate. For example, sensor data of the monitor device may contribute to determining the causes for the ostomy data measured on the base plate.

It is an advantage of the present disclosure that a user of an ostomy appliance or a health care professional is given herein improved tools to monitor and plan the use of the ostomy appliance with daily life by exploiting sensor data of a monitor device obtainable by the accessory device. The present disclosure provides an improved accuracy in monitoring and prediction of performance of an ostomy appliance with an improved degree of comfort for a user. The present disclosure permit deriving operating states in a more accurate manner by sensor data of monitor device that is seen as affecting the operating state. In other words, the disclosed method and accessory device allows to anticipate and indicate the dynamic internal of the base plate to a user, which supports the user in coordinating the use of the ostomy appliance with the planning of daily life activities.

An operating state of the base plate in the present disclosure is indicative of the dynamic internal state of the base plate of the ostomy appliance currently being worn by the user optionally related to adhesive performance of the base plate. Adhesive performance of the ostomy appliance may be related to an internal condition of the base plate of the ostomy appliance, such as an internal condition of an adhesive layer of the base plate. The adhesive performance, and thereby the operating state may be affected by several factors, such as humidity, temperature, misplacement of the ostomy appliance on the stoma, and/or malfunction of the ostomy appliance. The one or more factors alone or in combination impact the (current and/or future) adhesive performance of the base plate of the ostomy appliance. The operating state may be varying in time. The operating state may be indicative of a degree of erosion of the base plate.

Adhesive performance may be indicative of wear property, e.g. wear time and/or wear comfort. The operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate, such as of the first adhesive layer.

An operating state may be configured to indicate whether the ostomy appliance or the base plate thereof is properly operational based on its adhesive performance (e.g. wear property, e.g. wear time and/or wear comfort). For example, the operating state may be indicative of the severity and/or imminence of a leakage (e.g. low, medium, acute). The operating state may comprise Z operating states, where Z is an integer. The operating state may comprise a first operating state, a second operating state, and/or a third operating state (e.g. good, check, change in X time/NOW).

The processor may be configured to display, on the display, a first user interface comprising a first user interface object representing the operating state of the base plate in accordance with a display criterion being satisfied.

In the accessory device, to determine an operating state of the base plate based on the sensor data and one or more of ostomy data and parameter data based on ostomy data may comprise to determine an estimate of remaining wear time of the base plate, e.g. based on the sensor data and/or one or more of ostomy data and parameter data based on ostomy data. The first user interface object may represent the estimate of remaining wear time of the base plate.

In one or more exemplary accessory devices, the display criterion may be satisfied if the estimate of the remaining wear time of the base plate is less than a display threshold, such as less than 2 hours.

In the accessory device, to determine an estimate of remaining wear time of the base plate may comprise to determine a change in a current estimate of remaining wear time of the base plate. The estimate of estimate of remaining wear time of the base plate may be based on the current estimate of remaining wear time and the change in the current estimate of remaining wear time.

In the accessory device, to determine an estimate of remaining wear time of the base plate may comprise to increase a current estimate of remaining wear time of the base plate in accordance with a set of increase criteria being satisfied. The set of increase criteria may comprise one or more increase criteria.

In the accessory device, to determine an estimate of remaining wear time of the base plate may comprise to reduce a current estimate of remaining wear time of the base plate in accordance with a set of reduction criteria being satisfied. The set of reduction criteria may comprise one or more reduction criteria.

In the accessory device, at least a first increase criterion of the set of increase criteria may be based on the sensor data. A second increase criterion and/or a third increase criterion may be based on the sensor data. In the accessory device, at least a first increase criterion of the set of increase criteria may be based on the ostomy data and/or parameter data based on the ostomy data. A second increase criterion and/or a third increase criterion may be based on the ostomy data and/or parameter data based on the ostomy data.

The sensor data may comprise humidity data of a humidity sensor in the monitor device, and the operating state of the base plate is optionally based on the humidity data. Accordingly, one or more increase criteria of the set of increase criteria may be based on humidity data of the monitor device.

In one or more exemplary accessory devices, the processor is configured to increase a current estimate of remaining wear time of the base plate in accordance with a set of increase criteria being satisfied, wherein the set of increase criteria is satisfied if the humidity data is indicative of a humidity value larger than a first humidity threshold, e.g. for a first time period less than a first time threshold. Thus, an increase in humidity for a limited time period may contribute to an increased wear time of the base plate in turn increasing the estimate of remaining wear time of the base plate.

In one or more exemplary accessory devices, the processor is configured to increase a current estimate of remaining wear time of the base plate in accordance with a set of increase criteria being satisfied, wherein the set of increase criteria is satisfied if the humidity data is indicative of a humidity value less than a second humidity threshold, e.g. for a second time period larger than a second time threshold. Thus, a reduction in humidity for a second time period larger than a second time threshold may contribute to an increased wear time of the base plate in turn increasing the estimate of remaining wear time of the base plate.

In one or more exemplary accessory devices, the processor is configured to reduce a current estimate of remaining wear time of the base plate in accordance with a set of reduction criteria being satisfied, wherein the set of reduction criteria is satisfied if the humidity data is indicative of a humidity value larger than a third humidity threshold, e.g. for a third time period larger than a third time threshold. Thus, an increase in humidity for an extended time period may contribute to a reduction in wear time of the base plate in turn reducing the estimate of remaining wear time of the base plate.

The sensor data may comprise temperature data of a temperature sensor in the monitor device, and wherein the operating state of the base plate is optionally based on the temperature data. Accordingly, one or more increase criteria of the set of increase criteria may be based on temperature data of the monitor device.

In one or more exemplary accessory devices, the processor is configured to increase a current estimate of remaining wear time of the base plate in accordance with a set of increase criteria being satisfied, wherein the set of increase criteria is satisfied if the temperature data is indicative of a temperature value larger than a first temperature threshold, e.g. for a first time period less than a first time threshold. Thus, an increase in temperature for a limited time period may contribute to an increased wear time of the base plate in turn increasing the estimate of remaining wear time of the base plate.

In one or more exemplary accessory devices, the processor is configured to reduce a current estimate of remaining wear time of the base plate in accordance with a set of reduction criteria being satisfied, wherein the set of reduction criteria is satisfied if the temperature data is indicative of a temperature value larger than a third temperature threshold, e.g. for a third time period larger than a third time threshold. Thus, an increase in temperature for an extended time period may contribute to a reduction in wear time of the base plate in turn reducing the estimate of remaining wear time of the base plate.

The sensor data may comprise acceleration data of an accelerometer in the monitor device, and wherein the operating state of the base plate is based on the acceleration data. Accordingly, one or more increase criteria of the set of increase criteria may be based on acceleration data of the monitor device.

The sensor data may comprise gyroscope data of a gyroscope in the monitor device, and wherein the operating state of the base plate is based on the gyroscope data. Accordingly, one or more increase criteria of the set of increase criteria may be based on gyroscope data of the monitor device.

The sensor data may comprise magnetometer data of a magnetometer in the monitor device, and wherein the operating state of the base plate is based on the magnetometer data. Accordingly, one or more increase criteria of the set of increase criteria may be based on magnetometer data of the monitor device.

The acceleration data, gyroscope data and/or magnetometer data may be indicative of an activity level of a user. The processor may be configured to determine an activity level of a user, e.g. based on the acceleration data, gyroscope data and/or magnetometer data. Accordingly, one or more increase criteria of the set of increase criteria may be based on gyroscope data and/or magnetometer data of the monitor device. Experimental results have shown that a wear time of a base plate (and thus remaining wear time as an operating state of the base plate) may be affected negatively due to a high activity level (e.g. sports, bending, movement) by a reducing factor ranging from 2 to 10 compared to when the user has no or little activity (e.g. a sedentary user), For example, a total wear time may be reduced by a factor of 2 to 10 due to a high or extensive activity level, thus affecting the operating state of the base, e.g. remaining wear time.

In one or more exemplary accessory devices, the processor is configured to increase a current estimate of remaining wear time of the base plate in accordance with a set of increase criteria being satisfied, wherein the set of increase criteria is satisfied if the acceleration data, gyroscope data and/or magnetometer data are indicative of an activity level less than a first activity threshold, e.g. for a first time period larger than a first time threshold. Thus, a decrease in activity for an extended time period may contribute to an increased wear time of the base plate in turn increasing the estimate of remaining wear time of the base plate.

The first user interface object may be a notification, e.g. wherein the first user interface is a lock screen or a home screen of the accessory device.

The first user interface object may be an application launch icon and the first user interface may be a home screen.

The first user interface may be an application user interface of an application running on the accessory device.

Also disclosed is a method, performed in an accessory device of an ostomy system, wherein the accessory device comprises an interface configured to communicate with one or more devices of the ostomy system, the interface comprising a display, wherein the ostomy system comprises a monitor device and/or an ostomy appliance configured to be placed on a skin surface of a user, wherein the ostomy appliance comprises a base plate. The method comprises obtaining monitor data, the monitor data comprising sensor data and one or more of ostomy data obtained from electrodes of the base plate, and parameter data based on ostomy data obtained from electrodes of the base plate, the sensor data obtained from one or more sensors in the monitor device; determining an operating state of the base plate based on the sensor data and one or more of ostomy data and parameter data based on ostomy data; and displaying, on the display, a first user interface comprising a first user interface object representing the operating state of the base plate.

In the method, determining an operating state of the base plate based on the sensor data and one or more of ostomy data and parameter data based on ostomy data may comprise determining an estimate of remaining wear time of the base plate based on the sensor data and one or more of ostomy data and parameter data based on ostomy data, and wherein the first user interface object represents the estimate of remaining wear time of the base plate.

In the method, determining an estimate of remaining wear time of the base plate may comprise determining a change in a current estimate of remaining wear time of the base plate, wherein the estimate of estimate of remaining wear time of the base plate is based on the current estimate of remaining wear time and the change in the current estimate of remaining wear time.

In the method, determining an estimate of remaining wear time of the base plate may comprise increasing a current estimate of remaining wear time of the base plate in accordance with a set of increase criteria being satisfied.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The base plate 4 and the monitor device 6 are in a coupled state, and the monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. The monitor data may include sensor data of the monitor device. In the illustrated ostomy system, the accessory device 8 is a mobile phone or smartphone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
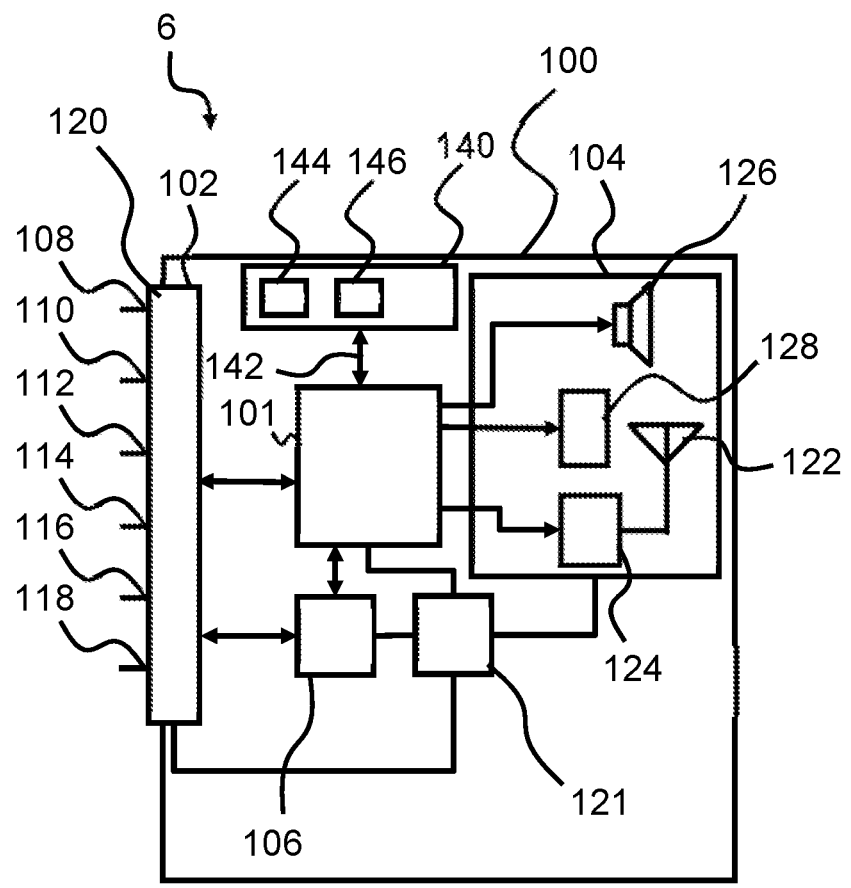
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101 for provision of sensor data 142 to the processor 101. The sensor unit 140 comprises a first sensor 144 being a temperature and humidity sensor for feeding temperature and humidity data as sensor data 142 to the processor 101. Further, the sensor unit 140 comprises a second sensor 146 being an accelerometer for feeding acceleration data as sensor data 142 to the processor 101. The processor 101 receives and stores sensor data 142 comprising temperature data, humidity data, and acceleration data, in the memory 106 and/or transmits the sensor data as part of monitor data via second interface 104.

The monitor device 100 is configured to obtain ostomy data from the base plate coupled to the first interface 102. The ostomy data may be stored in the memory 106 and/or processed in the processor 101 in order to obtain parameter data based on the ostomy data.

Figure 3:
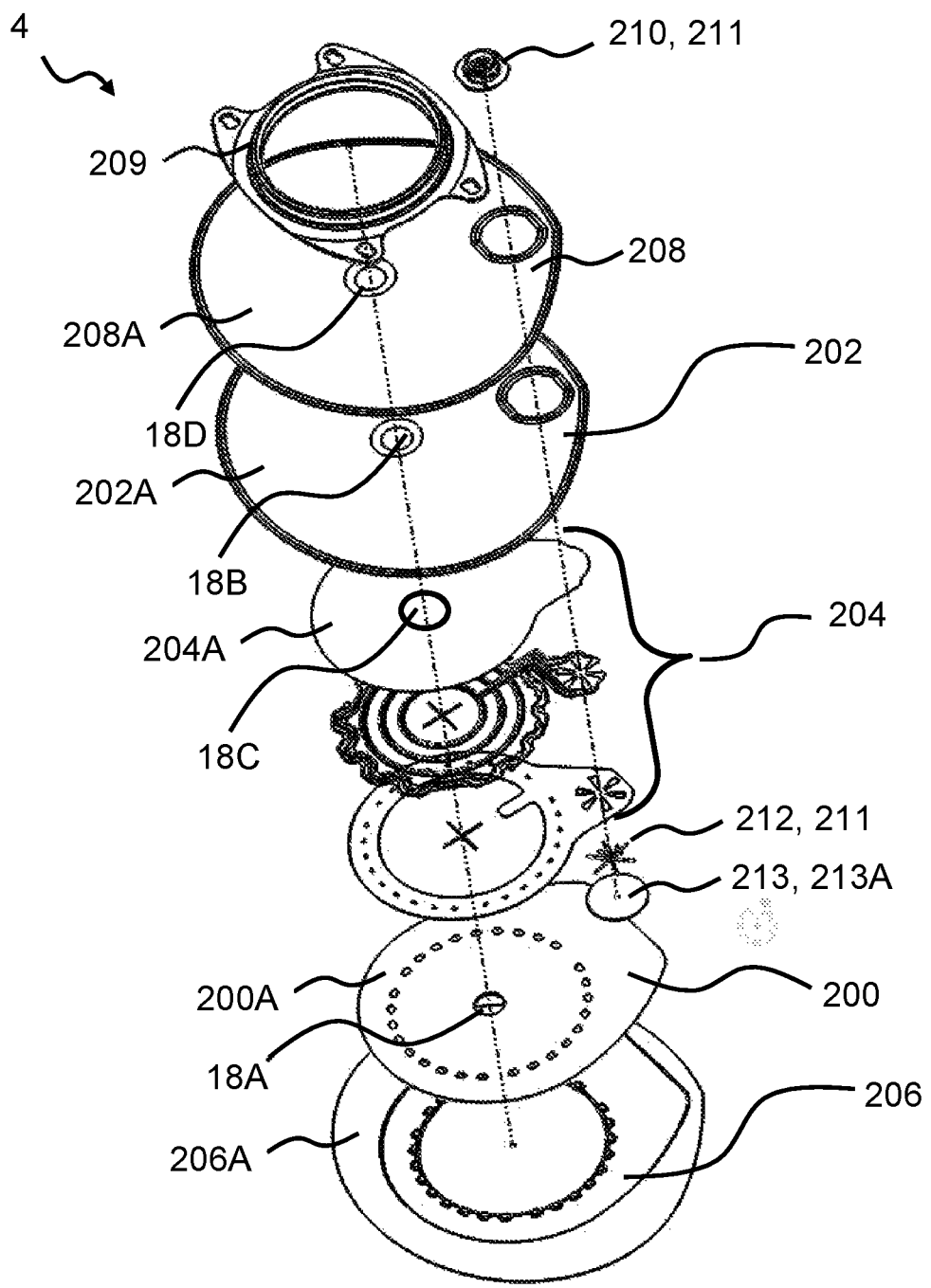
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202 with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
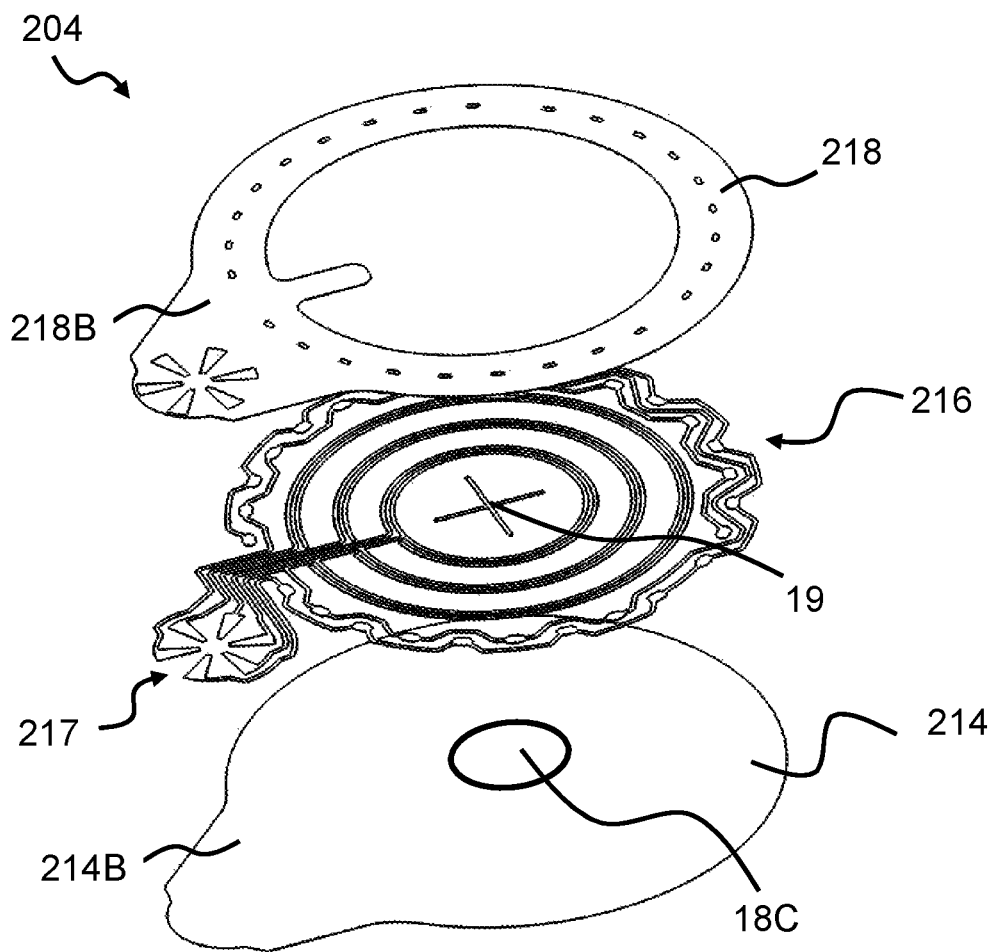
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
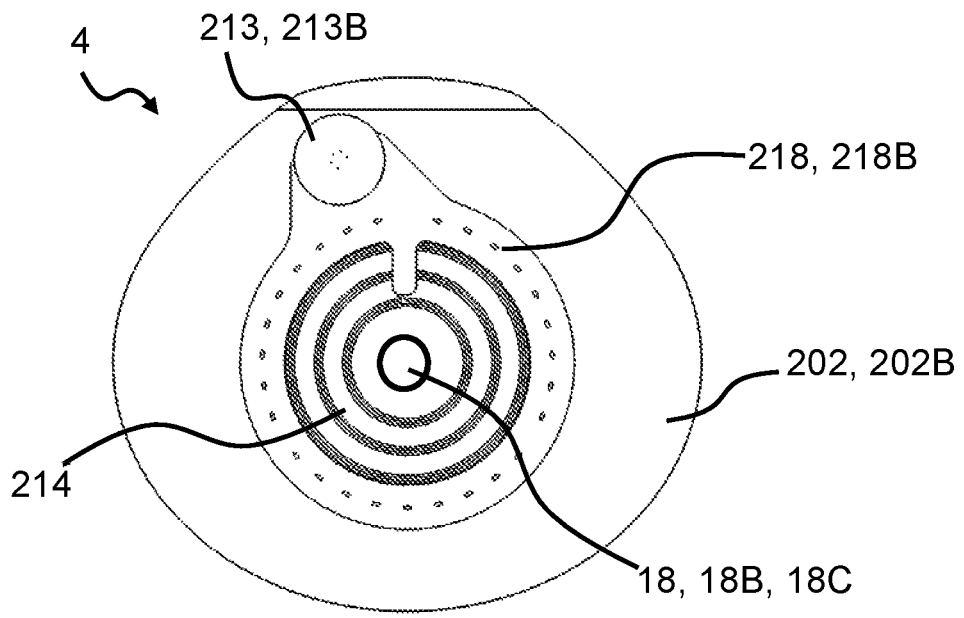
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
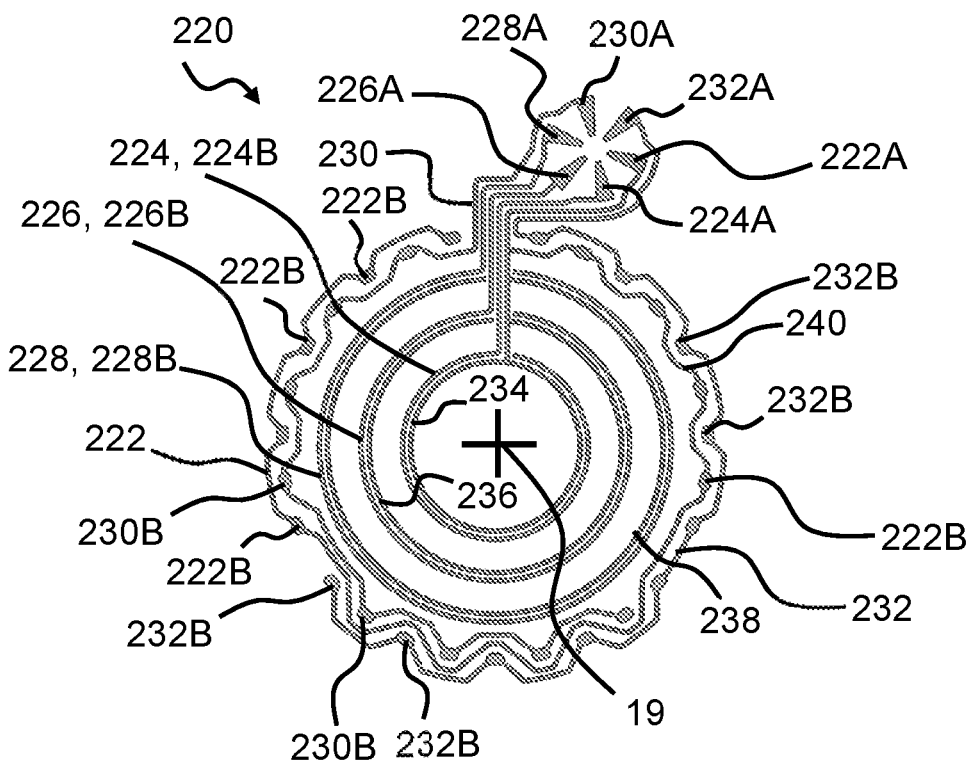
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 may be around 14 mm. In one or more embodiments, the first radial distance R1 may be around 13 mm, such as 12.5 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 may be 18 mm. In one or more embodiments, the second radial distance R2 may be 17 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. In one or more embodiments, the third radial distance R3 is 21 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point (such as a leakage radius R5 which may be around 32 mmm from the center point). The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

Figure 7:
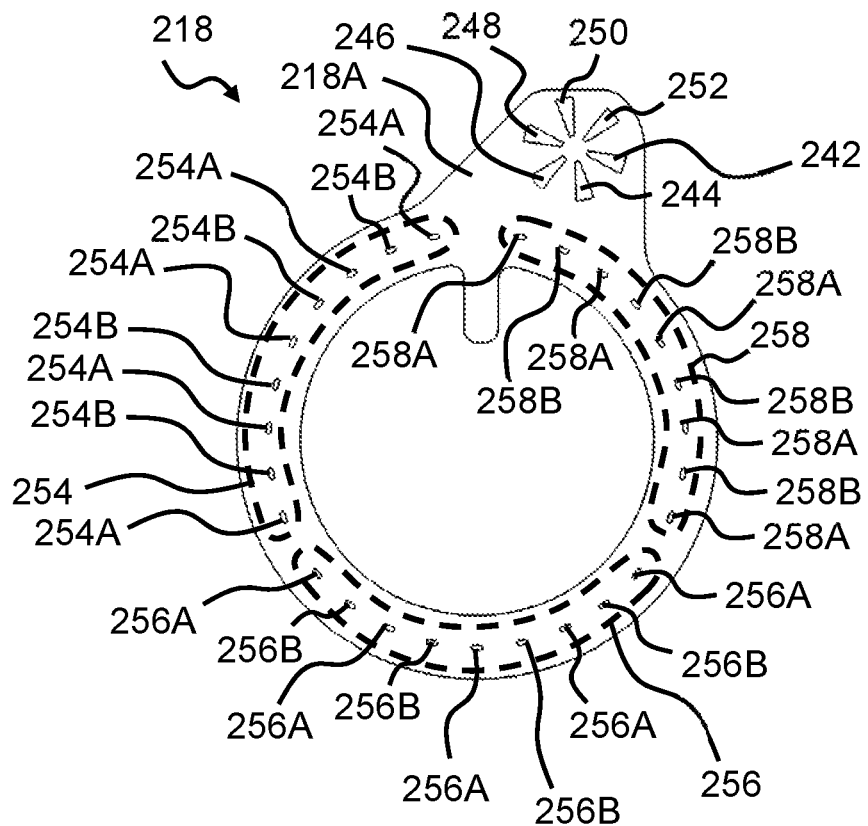
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
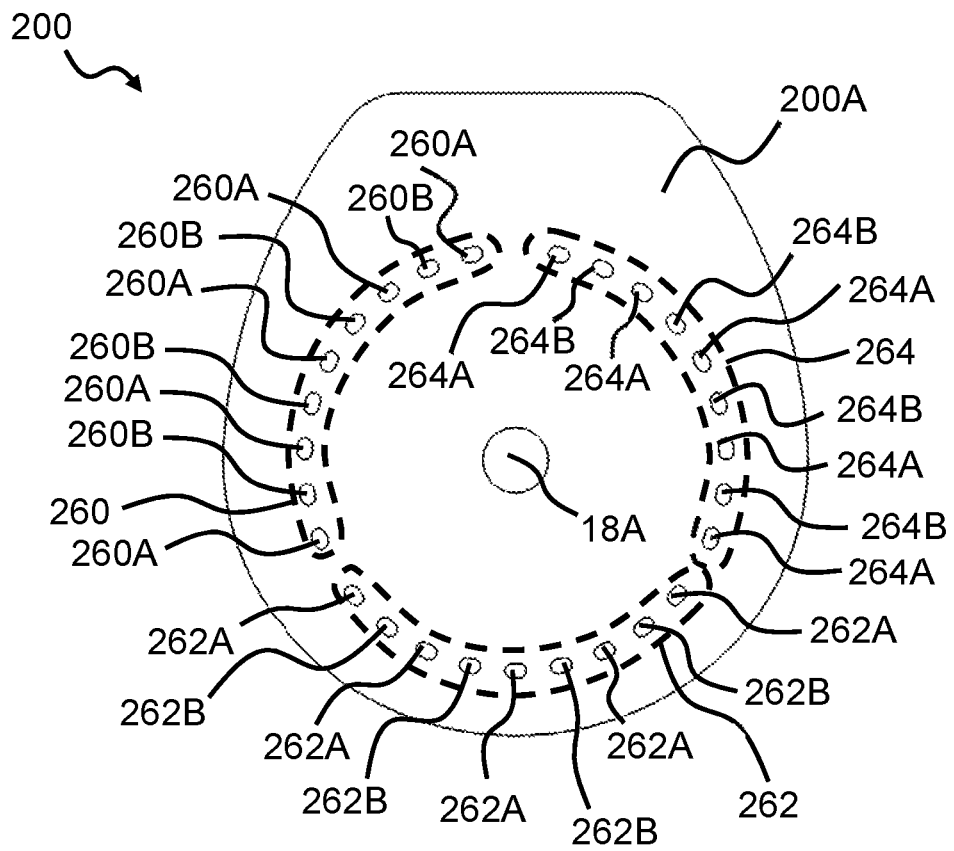
FIG. 8 is a distal view of an exemplary first adhesive layer.
Figure 9:
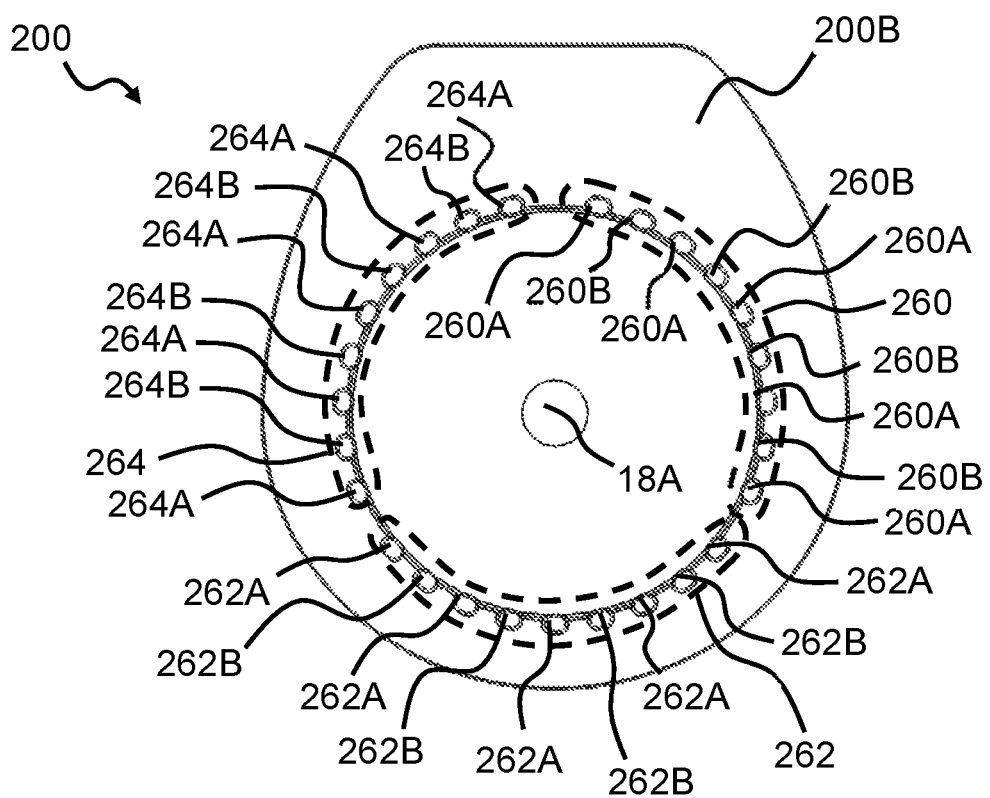
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary first sensor point openings 260A each configured to overlap a part of the ground electrode 222. The primary sensor point openings comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary first sensor point openings 262A each configured to overlap a part of the fifth electrode 232. The secondary sensor point openings comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary first sensor point openings 264A each configured to overlap a part of the fifth electrode 232. The tertiary sensor point openings comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
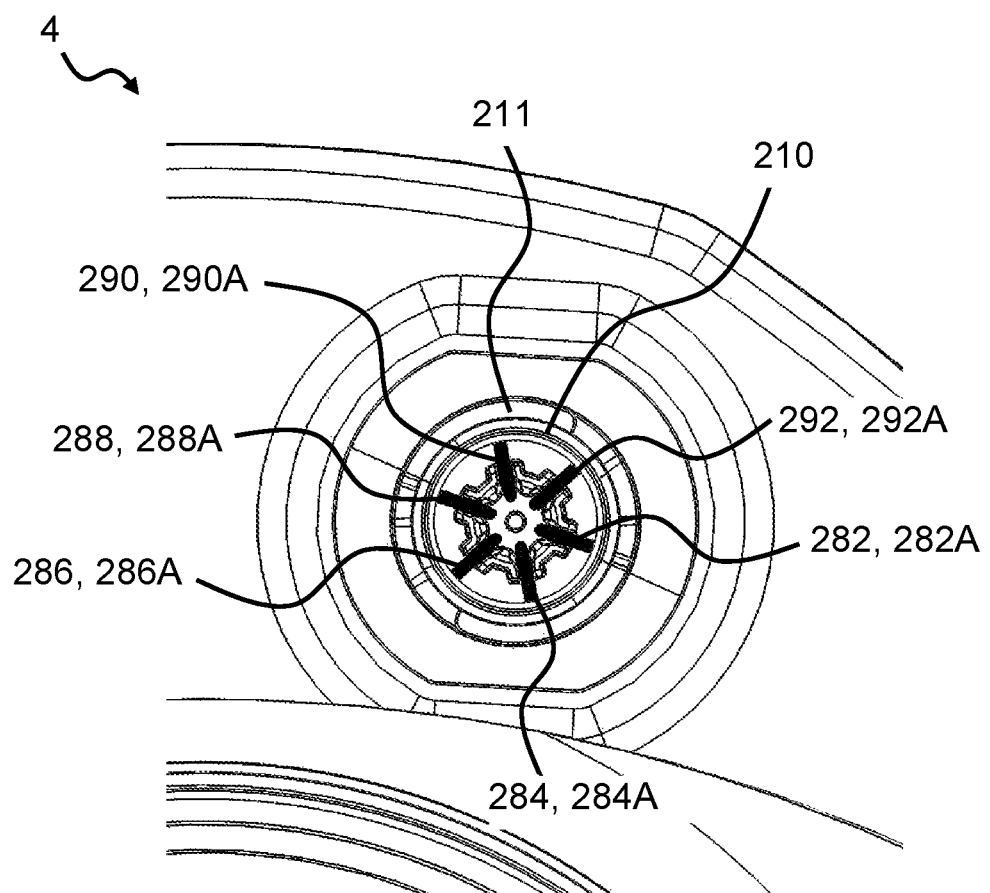
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
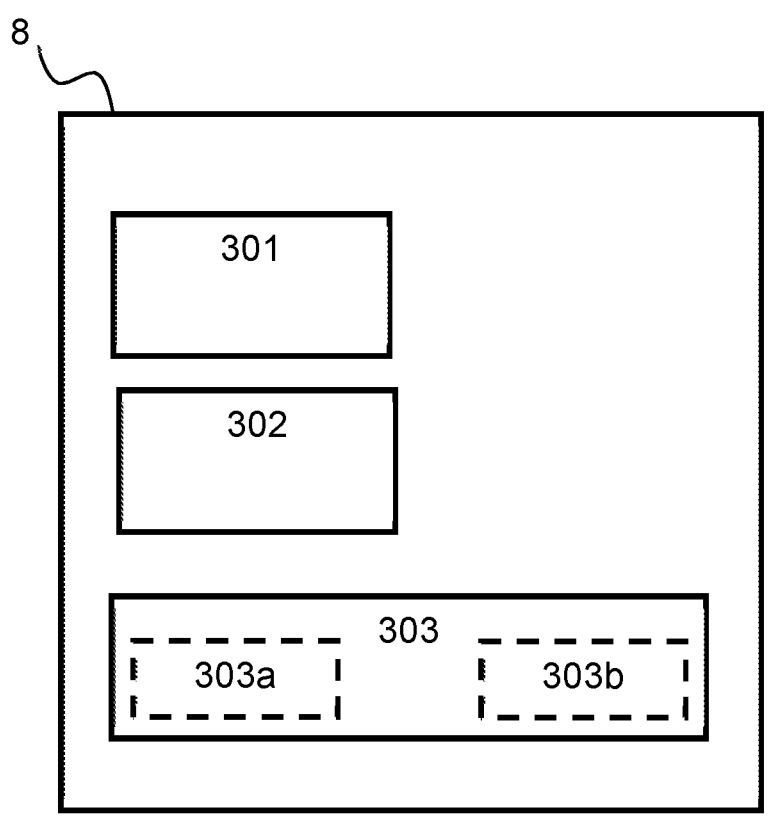
FIG. 11 illustrates an exemplary accessory device according to the present disclosure.

FIG. 11 is a block diagram illustrating an exemplary accessory device 8 according to the present disclosure. The accessory device 8 forms part of an ostomy system 1 and is capable of determining of the operating states of an ostomy appliance 2 to be placed on a user's skin, in particular the determining of an operating state of the base plate 4 of the ostomy appliance based on sensor data of monitor device 6, see FIG. 1. The accessory device 8 comprises a memory 301; a processor 302 coupled to the memory 301; and an interface 303 coupled to the processor 302.

The interface 303 is configured to communicate with monitor device, wherein the interface comprises a display 303a and is configured to obtain monitor data from the monitor device coupled to the ostomy appliance, the monitor data comprising sensor data and one or more of ostomy data obtained from electrodes of the base plate, and parameter data based on ostomy data obtained from electrodes of the base plate, the sensor data obtained from one or more sensors in the monitor device. The monitor data or at least parts thereof may be stored in the memory 301.

Figure 12:
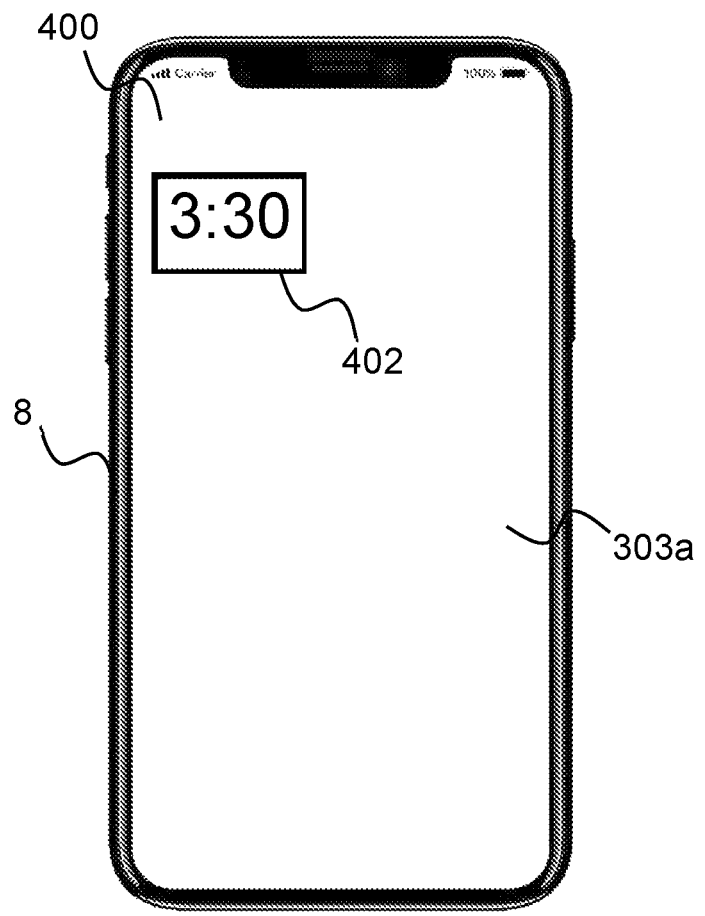
FIG. 12 illustrates an exemplary accessory device according to the present disclosure.

The processor 302 is configured to determine an operating state of the base plate based on the sensor data and one or more of ostomy data and parameter data based on ostomy data; and display, on the display 303a, a first user interface 400 comprising a first user interface object 402 representing the operating state of the base plate, see FIG. 12.

The processor 302 is configured to communicate with one or more devices of the ostomy system. The one or more devices comprise a monitor device disclosed herein, and/or an ostomy appliance configured to be placed on a skin surface of a user or on any additional seals. The ostomy appliance comprises a base plate. The base plate may comprise a first adhesive layer having a proximal side. During use, a proximal surface of the first adhesive layer adheres to the user's skin in the peristomal area and/or to additional seals, such as sealing paste, sealing tape and/or sealing ring. The base plate may comprise one or more electrodes configured to measure electrical properties of the first adhesive layer. The electrical properties may be indicative of a conductive path in the first adhesive layer, thereby indicative of the moisture level, and indicative of the condition of the base plate of the ostomy appliance.

The interface 303 comprises a display 303a and a transceiver unit 303b comprising a transceiver and an antenna. The interface 303 is configured to obtain monitor data from the monitor device, such as to receive or retrieve the monitor data from the monitor device. The transceiver unit 303b may be configured to obtain monitor data from the one or more devices, e.g. from the monitor device.

The interface 303 is configured to obtain monitor data from the one or more devices. The monitor data may be indicative of a condition of the ostomy appliance, such as a condition of a proximal side of a layer of the ostomy appliance (e.g. a first adhesive layer of the base plate) that is directed towards the skin surface.

The processor 302 is configured to determine an operating state of the base plate based on the sensor data and one or more of ostomy data and parameter data based on ostomy data; and display, on the display 303a, a first user interface comprising a first user interface object representing the operating state of the base plate. The accessory device may be configured to communicate the operating state, via the display 303a or the transceiver unit 303b, e.g. to the user, and/or to other devices.

In the accessory device 8, to determine an operating state of the base plate based on the sensor data and one or more of ostomy data and parameter data based on ostomy data optionally comprises to determine an estimate of remaining wear time of the base plate based on the sensor data and one or more of ostomy data and parameter data based on ostomy data, and wherein the first user interface object represents the estimate of remaining wear time of the base plate. To determine an estimate of remaining wear time of the base plate comprises to determine a change in a current estimate of remaining wear time of the base plate, wherein the estimate of remaining wear time of the base plate is based on the current estimate of remaining wear time and the change in the current estimate of remaining wear time. Further, to determine an estimate of remaining wear time of the base plate comprises to increase a current estimate of remaining wear time of the base plate in accordance with a set of increase criteria being satisfied. At least a first increase criterion of the set of increase criteria is optionally based on the sensor data. The sensor data optionally comprises humidity data of a humidity sensor in the monitor device, and the operating state of the base plate is based on the humidity data.

The sensor data optionally comprises temperature data of a temperature sensor in the monitor device, and the operating state of the base plate is based on the temperature data.

The processor 302 may be configured to determine the operating state of the base plate based on the sensor data and one or more of ostomy data and parameter data based on ostomy data by determining a current moisture pattern type based on the ostomy data and/or parameter data based on the ostomy data, and by generating the operating state based on the current moisture pattern types and the sensor data of the monitor device.

Determining a current moisture pattern type may be based on the ostomy data and/or the parameter data (e.g. first parameter data and second parameter data), such as based on measurements obtained by the electrodes, such as measurements of resistance, capacitance and/or inductance, such as timing information.

The processor 302 may be configured to determine the operating state based on a current operating state, and optionally any prior operating state prior to the determining of the operating state.

To determine an operating state of the base plate of the ostomy appliance may comprise to determine an operating state from a set of operating states. In other words, to determine an operating state may comprise selecting an operating state from a set of predefined operating states based on the sensor data and one or more of ostomy data and parameter data based on ostomy data. The set of predefined operating states may comprise a number of operating states, such as at least two operating states, at least three operating states, at least four operating states, at least five operating states. The number of operating states may be in the range from four to twenty. In one or more exemplary accessory devices, the number of operating states in the set of predefined operating states is larger than ten, such as larger than 20 or even larger than 50.

The processor 302 may be configured to display, on the display, a first user interface comprising a first user interface object representing the operating state of the base plate.

The processor 302 may be configured to display, on the display, a first user interface comprising a first user interface object representing the operating state of the base plate by notifying the user via the interface 303, such as by displaying a notification on display 303a of the accessory device 8. The notification may comprise the first user interface object representative of the operating state. The notification may comprise a notification indicator to open an application related to the ostomy appliance.

FIG. 12 shows an exemplary accessory device 8 displaying a first user interface 400 on display 303a. The first user interface 400 comprises first user interface object 402 representing an estimate of remaining wear time (3 hours and 30 minutes) determined by the processor of the accessory device 8.

Figure 13:
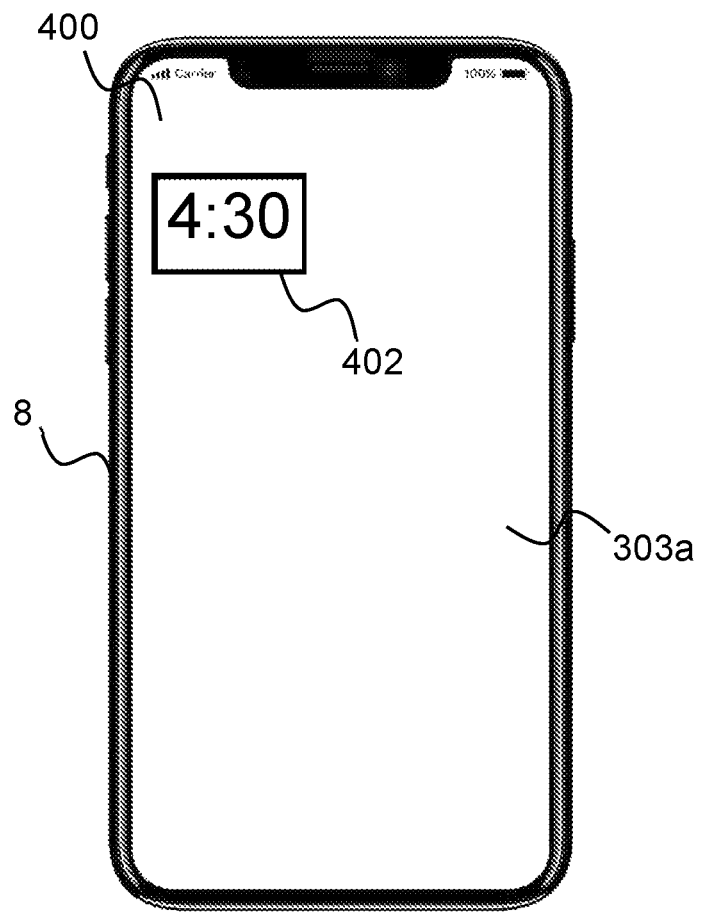
FIG. 13 illustrates an exemplary accessory device according to the present disclosure.

FIG. 13 shows an exemplary accessory device 8. The processor of accessory device 8 has determined a change of 1 hour in a current estimate of remaining wear time of 3 hours and 30 minutes and has determined an estimate of remaining wear time as a sum of the current estimate and the change to obtain an estimate of remaining wear time of 4 hours and 30 minutes, which is represented by the first user interface object 402 of the first user interface 400.

Figure 14:
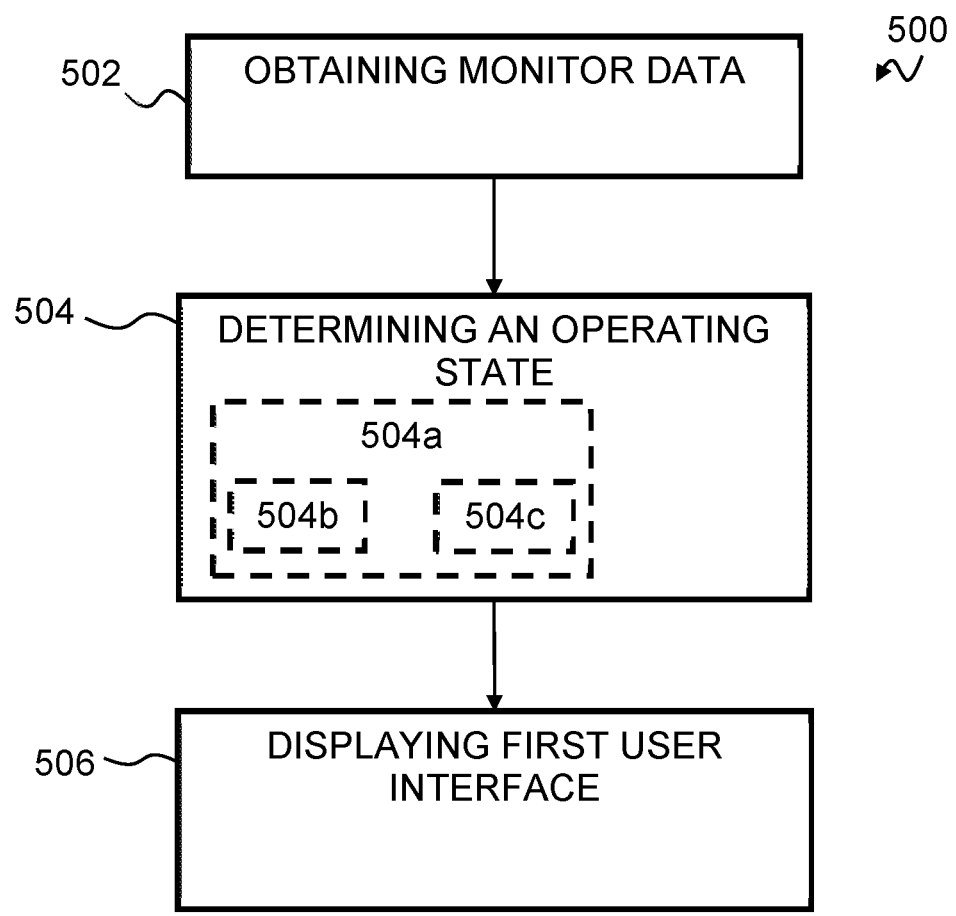
FIG. 14 illustrates an exemplary method according to the present disclosure.

FIG. 14 shows a flow diagram of an exemplary method. The method 500 is performed in an accessory device of an ostomy system, e.g. accessory device 8 of ostomy system 1, wherein the accessory device comprises an interface configured to communicate with one or more devices of the ostomy system, the interface comprising a display, wherein the ostomy system comprises a monitor device and/or an ostomy appliance configured to be placed on a skin surface of a user, wherein the ostomy appliance comprises a base plate, the method 500 comprising obtaining 502 monitor data, the monitor data comprising sensor data and one or more of ostomy data obtained from electrodes of the base plate, and parameter data based on ostomy data obtained from electrodes of the base plate, the sensor data obtained from one or more sensors in the monitor device; determining 504 an operating state of the base plate based on the sensor data and one or more of ostomy data and parameter data based on ostomy data; and displaying 506, on the display, a first user interface comprising a first user interface object representing the operating state of the base plate.

In the method 500, determining 504 an operating state of the base plate based on the sensor data and one or more of ostomy data and parameter data based on ostomy data comprises determining 504a an estimate of remaining wear time of the base plate based on the sensor data and one or more of ostomy data and parameter data based on ostomy data, and wherein the first user interface object represents the estimate of remaining wear time of the base plate.

Optionally, determining 504a an estimate of remaining wear time of the base plate comprises determining 504b a change in a current estimate of remaining wear time of the base plate, wherein the estimate of estimate of remaining wear time of the base plate is based on the current estimate of remaining wear time and the change in the current estimate of remaining wear time. Further, determining 504a an estimate of remaining wear time of the base plate optionally comprises increasing 504c a current estimate of remaining wear time of the base plate, e.g. in accordance with a set of increase criteria being satisfied.

Figure 15A:
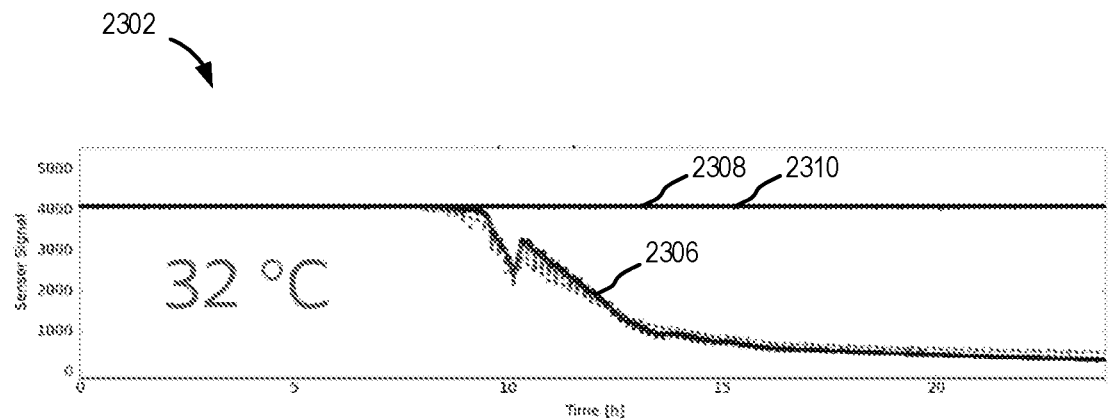
FIGS. 15A-15B are exemplary graphical representations of parameter data as functions of time for different predetermined temperatures.

FIG. 15A shows an exemplary graphical representation 2302 of parameter data as a function of time for a first type of base plate at a first predetermined temperature. The first predetermined temperature in the example depicted in FIG. 15A is 32 degrees Celsius.

Figure 15B:
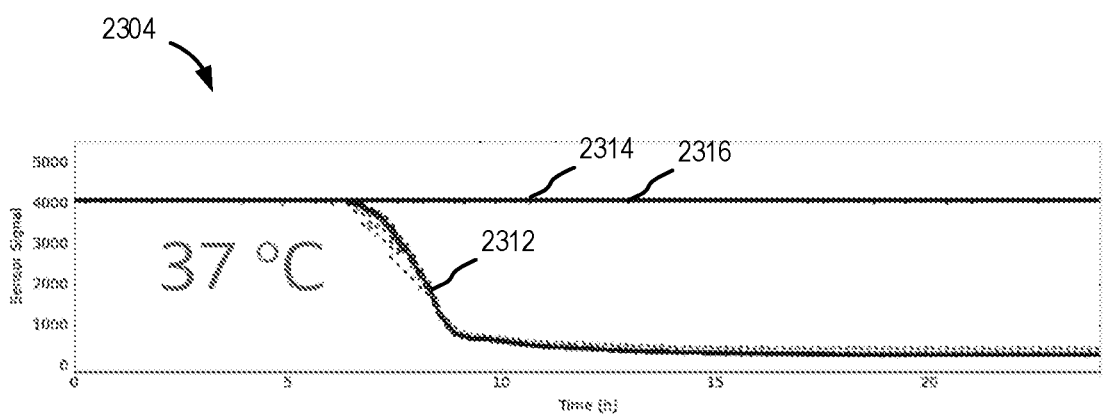

FIG. 15B shows an exemplary graphical representation 2304 of parameter data as a function of time for the first type of base plate at a second predetermined temperature. The second predetermined temperature in the example depicted in FIG. 15B is 37 degrees Celsius. The temperatures were selected to closely approximate human skin temperature.

FIGS. 15A and 15B were obtained by applying fluid at a stomal opening of a base plate, wherein the stomal opening had a diameter of 22 mm. The residual humidity of the environment for both experiments was 50%. As the fluid was absorbed by the base plate over time and the fluid propagated radially from the stomal opening outward, parameter data (e.g. voltages (mV)) was measured between a first electrode pair, a second electrode pair, and/or a third electrode pair respectively.

Specifically, in FIG. 15A, curve 2306 shows, as a function of time, a decrease in voltage for the first electrode pair at approximately 8.3 hours. Curve 2308 shows, as a function of time, a constant voltage for the second electrode pair. And, curve 2310 shows, as a function of time, a constant voltage for the third electrode pair.

By comparison, in FIG. 15B, curve 2312 shows a decrease in voltage for the first electrode pair at approximately 7.6 hours. Curve, 2314 shows, as a function of time, a constant voltage for the second electrode pair. And, curve 2316 shows, as a function of time, a constant voltage for the third electrode pair.

Stated another way, in this example, moisture propagated approximately 11% faster when the temperature was 37 degrees Celsius in comparison to when the temperature was 32 degrees Celsius. This comparison shows that as temperature increases, wear time of the base plate decreases due to faster moisture propagation and adhesion degradation.

Another experiment was conducted where the propagation speed of fluid, applied at the stomal opening of a second type of base plate, was measured. Similar to the experiment depicted in FIGS. 15A, 15B, the stomal opening had a diameter of 22 mm and the residual humidity of the environment was 50%. The second type of base plate is different than the first type of base plate, in that the composition of the first adhesive layer of the first type of base plate is different than the composition of the first adhesive layer of the second type of base plate.

In this experiment, the fluid propagated between center of the hole and first electrode pair at approximately 0.15 mm/hour when the temperature was 32 degrees Celsius. In comparison, the fluid propagated at approximately 0.2 mm/hour when the temperature was 37 degrees Celsius. As such, this experiment similarly found that for another type of base plate as temperature increases, wear time of the second type of base plate decreases due to faster moisture propagation and adhesion degradation.

In view of the above results, a scaling factor may be applied to the operating state (e.g. wear time) of a base plate such that the scaling factor affects negatively the operating state (e.g. decreases the wear time) of the base plate as temperature increases and/or the scaling factor affects positively the operating state (e.g. increases the wear time) of the base plate as temperature decreases.

In some embodiments, the scaling factor may be predetermined. In these embodiments, the predetermined scaling factor may be constant. Alternatively, the predetermined scaling factor may be iteratively adjusted based on when the first electrode pair, the second electrode pair, and/or the third electrode pair are triggered. In at least some of these embodiments, the predetermined scaling factor may be iteratively adjusted.

The use of the terms "first", "second", "third" and "fourth", "primary", "secondary", "tertiary" etc. does not imply any particular order but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part 121 power unit
122 antenna
124 wireless transceiver
126 loudspeaker
128 haptic feedback element
140 sensor unit
142 sensor data
144 first sensor
146 second sensor
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode
222A ground connection part
222B ground sensing part
222C ground connector part
224 first electrode
224A first connection part
224B first sensing part
224C first conductor part
226 second electrode
226A second connection part
226B second sensing part
226C second conductor part
228 third electrode
228A third connection part
228B third sensing part
228C third conductor part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
301 memory
302 processor
303 interface
303a display
303b transceiver unit
400 first user interface
402 first user interface object
500 method
502 obtaining monitor data
504 determining operating state
504a determining remaining wear time
504b determining a change in a current estimate of remaining wear time
504c increasing a current estimate of remaining wear time of the base plate
506 displaying first user interface
2302 a graphical representation of parameter data as a function of time at a first predetermined temperature
2304 a graphical representation of parameter data as a function of time at a second predetermined temperature
2306 curve showing, as a function of time, a decrease in voltage for the first electrode pair at a first predetermined temperature
2308 curve showing, as a function of time, a constant voltage for the second electrode pair at the first predetermined temperature
2310 curve showing, as a function of time, a constant voltage for the third electrode pair at the first predetermined temperature 2312 curve showing, as a function of time, a decrease in voltage for the first electrode pair at a second predetermined temperature 2314 curve showing, as a function of time, a constant voltage for the second electrode pair at the second predetermined temperature 2316 curve showing, as a function of time, a constant voltage for the third electrode pair at the second predetermined temperature

The invention claimed is:

1. An accessory device for an ostomy system comprising a monitor device and an ostomy appliance, the ostomy appliance comprising a base plate comprising a first adhesive layer and one or more electrodes, the accessory device comprising:
    a memory;
    a processor; and
    an interface coupled to the processor and configured to communicate with the monitor device, wherein the monitor device is configured to be coupled to the base plate to obtain ostomy data from the one or more electrodes of the base plate, and wherein the interface comprises a display and is configured to obtain monitor data from the monitor device, the monitor data comprising sensor data and one or more of ostomy data obtained from the one or more electrodes of the base plate, and parameter data based on the ostomy data obtained from the one or more electrodes of the base plate, the ostomy data being indicative of electrical properties including a conductive path in the first adhesive layer of the base plate, the sensor data being obtained from one or more sensors in the monitor device,
    wherein the processor is configured to:
    determine, based on the sensor data and the one or more of the ostomy data and the parameter data based on the ostomy data, a current estimate of remaining wear time of the base plate and a change in the current estimate of remaining wear time of the base plate;
    determine an operating state of the base plate based on the current estimate of remaining wear time of the base plate and the change in the current estimate of remaining wear time of the base plate; and
    display, on the display, a first user interface comprising a first user interface object representing the operating state of the base plate.

2. The accessory device according to claim 1, wherein to determine the change in the current estimate of remaining wear time of the base plate comprises to increase the current estimate of remaining wear time of the base plate in accordance with a set of increase criteria being satisfied.

3. The accessory device according to claim 2, wherein at least a first increase criterion of the set of increase criteria is based on the sensor data.

4. The accessory device according to claim 1, wherein the sensor data comprises humidity data of a humidity sensor in the monitor device, and wherein the operating state of the base plate is based on the humidity data.

5. The accessory device according to claim 1, wherein the sensor data comprises temperature data of a temperature sensor in the monitor device, and wherein the operating state of the base plate is based on the temperature data.

6. The accessory device according to claim 1, wherein the sensor data comprises gyroscope data of a gyroscope in the monitor device, and wherein the operating state of the base plate is based on the gyroscope data.

7. The accessory device according to claim 1, wherein the sensor data comprises magnetometer data of a magnetometer in the monitor device, and wherein the operating state of the base plate is based on the magnetometer data.

8. The accessory device according to claim 1, wherein the first user interface object is a notification.

9. The accessory device according to claim 1, wherein the first user interface object is an application launch icon and the first user interface is a home screen.

10. A method, performed in an accessory device of an ostomy a system, wherein the accessory device comprises an interface configured to communicate with a monitor device of the ostomy system, the interface comprising a display, wherein the ostomy system comprises an ostomy appliance comprising a base plate comprising a first adhesive layer and one or more electrodes, wherein the monitor device is configured to be coupled to the base plate to obtain ostomy data from the one or more electrodes of the base plate, the method comprising:
    obtaining monitor data, the monitor data comprising sensor data and one or more of ostomy data obtained from the one or more electrodes of the base plate, and parameter data based on the ostomy data obtained from the one or more electrodes of the base plate, the ostomy data being indicative of electrical properties including a conductive path in the first adhesive layer of the base plate, and the sensor data being obtained from one or more sensors in the monitor device;
    determining, based on the sensor data and the one or more of the ostomy data and the parameter data based on the ostomy data, a current estimate of remaining wear time of the base plate and a change in the current estimate of remaining wear time of the base plate;
    determining an operating state of the base plate based on the current estimate of remaining wear time of the base plate and the change in the current estimate of remaining wear time of the base plate; and
    displaying, on the display, a first user interface comprising a first user interface object representing the operating state of the base plate.

11. The method according to claim 10, wherein determining the change in the current estimate of remaining wear time of the base plate comprises increasing the current estimate of remaining wear time of the base plate in accordance with a set of increase criteria being satisfied.

12. An accessory device for an ostomy system comprising a monitor device and an ostomy appliance, the ostomy appliance comprising a base plate comprising a first adhesive layer and one or more electrodes, the accessory device comprising:
    a memory;
    a processor; and
    an interface coupled to the processor and configured to communicate with the monitor device, wherein the monitor device is configured to be coupled to the base plate to obtain ostomy data from the one or more electrodes of the base plate, and wherein the interface comprises a display and is configured to obtain monitor data from the monitor device, the monitor data comprising sensor data and one or more of ostomy data obtained from the one or more electrodes of the base plate, and parameter data based on the ostomy data obtained from the one or more electrodes of the base plate, the ostomy data being indicative of electrical properties of the first adhesive layer of the base plate, the sensor data being obtained from one or more sensors in the monitor device, wherein the processor is configured to:
determine a current estimate of remaining wear time of the base plate based on the sensor data and the one or more of the ostomy data and the parameter data based on ostomy data;
determine an operating state of the base plate by increasing the current estimate of remaining wear time of the base plate in accordance with a set of increase criteria being satisfied; and
display, on the display, a first user interface comprising a first user interface object representing the operating state of the base plate.

* * * * *